(12) United States Patent
Scheuering

(10) Patent No.: US 7,054,412 B2
(45) Date of Patent: May 30, 2006

(54) METHOD AND X-RAY APPARATUS FOR DETERMINING THE X-RAY DOSE IN AN X-RAY EXAMINATION

(75) Inventor: Peter Scheuering, Fürth (DE)

(73) Assignee: Siemens Aktiengesellschaft, Munich (DE)

( * ) Notice: Subject to any disclaimer, the term of this patent is extended or adjusted under 35 U.S.C. 154(b) by 101 days.

(21) Appl. No.: 10/845,890

(22) Filed: May 14, 2004

(65) Prior Publication Data
US 2005/0013407 A1 Jan. 20, 2005

(30) Foreign Application Priority Data
May 16, 2003 (DE) ................................ 103 22 142

(51) Int. Cl.
*H05G 1/42* (2006.01)
(52) U.S. Cl. .................... 378/108; 378/96; 378/97; 378/98.7; 378/165; 378/166; 378/207
(58) Field of Classification Search ............... 378/16, 378/96, 97, 98.7, 108–112, 162, 165, 166, 378/205–207
See application file for complete search history.

(56) References Cited

U.S. PATENT DOCUMENTS

| 4,896,343 | A | * | 1/1990 | Saunders | ...................... 378/95 |
| 5,400,378 | A | * | 3/1995 | Toth | .............................. 378/16 |
| 5,446,780 | A | * | 8/1995 | Aichinger et al. | ........... 378/204 |
| 6,233,310 | B1 | * | 5/2001 | Relihan et al. | .............. 378/108 |
| 6,272,368 | B1 | * | 8/2001 | Alexandrescu | ............... 600/407 |
| 6,502,984 | B1 | * | 1/2003 | Kawasaki et al. | ........... 378/206 |
| 6,821,017 | B1 | * | 11/2004 | Tankersley | .................. 378/207 |
| 6,934,362 | B1 | * | 8/2005 | Scheuering | ................... 378/108 |
| 2003/0185349 | A1 | * | 10/2003 | Roeckseisen | ............... 378/206 |

FOREIGN PATENT DOCUMENTS

| DE | 38 10 501 | 2/1996 |
| DE | 197 30 519 | 1/1999 |

OTHER PUBLICATIONS

"Radiation Dosimetry For Extremity Radiographs," Huda et al, Health Physics (1998), vol. 75, No. 5, pp. 492-499.
Durchleuchtungsanlagen, Ein RXM-Vertriebshandbuch, Siemens AG (1992), pp. 24-26.
"Röntgen-aufnahmetechnik," Siemens AG (1991) pp. 125-127.

* cited by examiner

*Primary Examiner*—Allen C. Ho
(74) *Attorney, Agent, or Firm*—Schiff Hardin LLP

(57) ABSTRACT

In an x-ray apparatus and method to determine the radiation dose in x-ray examinations, the x-ray apparatus has an x-ray radiator, an automatic exposure timer, and a laser range finder to detect the focus-patient separation between the x-ray radiator and a patient, and a computer device determines the necessary radiation dose using the thickness of the body part of the patient to be examined. The thickness is calculated from the acquired focus-patient distance and geometric data of the x-ray apparatus.

9 Claims, 1 Drawing Sheet

METHOD AND X-RAY APPARATUS FOR DETERMINING THE X-RAY DOSE IN AN X-RAY EXAMINATION

BACKGROUND OF THE INVENTION

1. Field of the Invention

The present invention concerns an x-ray apparatus of the type having an x-ray radiator, an automatic exposure timer, and a laser range finder (distance meter) to detect the focus-patient separation between the x-ray radiator and a patient.

2. Description of the Prior Art

An x-ray apparatus of the above type is known from German OS 38 10 501. It is proposed therein to arrange a contact-less range finder near the x-ray radiator in order to measure the distance (FOBJ) between the x-ray radiator and the surface of the patient. The necessary incident dose power is subsequently determined using the measured distance. If one likewise considers the film-focus separation (FFA), which is a known quantity, the total separation between the surface of the patient and an x-ray film cassette can be determined. This known x-ray apparatus, however, does not enable the actual thickness of the patient to be determined. The necessary incident dose power therefore can be determined only approximately.

X-ray apparatuses, in particular surface body detector systems, possess in the majority of cases an exposure control or an automatic exposure timer. Conventional exposure controls have, for example, three measurement fields in order to produce x-ray exposures of the left or right extremities of the patient or of the central body. A disadvantage is that the measurement chambers are visible in the x-ray image, primarily in the exposure of thin subjects. This problem in particular occurs when obtaining x-rays of children, The artifacts thereby generated are perceived as disturbing by the radiologists and are therefore undesirable.

SUMMARY OF THE INVENTION

An object of the invention is to provide an x-ray apparatus that enables a more precise determination of the radiation dose, such that artifacts are prevented in the x-ray image.

This object is achieved in accordance with the invention by an x-ray apparatus of the type initially described wherein a computer device is provided to determine the necessary radiation dose using the thickness of the body part of the patient to be examined, the thickness being calculated from the acquired focus-patient distance and geometric data of the x-ray apparatus.

The invention is based on the recognition that it is possible to use the thickness or, respectively, the height of the body part of the patient to be examined for the calculation of the radiation dose. For this, it is first necessary to measure the distance between the x-ray radiator or focus and the patient. This measurement ensues with a laser range finder that is disposed in the region of the x-ray radiator. The x-ray apparatus has a computer device to determine the thickness of the body part of the patient to be examined from the acquired focus-patient distance and geometric data of the system. The distance between the focus or x-ray radiator and a film or image intensifier input screen of the x-ray apparatus is variable, but known. Also known is the thickness of the table top of the patient table and the thickness of the patient support. With such known geometric data, the sought height or thickness of the patient can be determined by the computer device.

The computer device of the inventive x-ray apparatus is fashioned to determine the necessary radiation dose using the determined thickness of the body part of the patient to be examined. The thickness of the patient is proportional to the necessary dose requirement. The necessary radiation dose can be correspondingly specified given known patient thickness, After the determination of the patient thickness, the necessary radiation dose is taken by the computer device from the reference table and the x-ray apparatus is correspondingly controlled, The invention also concerns a method to determine the radiation dose in x-ray examinations, including the steps of measurement of the focus-patient distance between the x-ray radiator and the patient with a laser range finder, calculation of the thickness of the body part of the patient to be examined from the measured distance and geometric data of the x-ray apparatus, and setting of the radiation dose dependent on the calculated thickness.

The radiation dose is appropriately taken from the reference table in the inventive method, but it is alternatively possible to determine the radiation dose using an approximation function.

In the method, the laser range finder can determine the highest point of the body part of the patient to be examined. The determined highest point is used as a value for the thickness to which the radiation dose is adapted.

In an embodiment of the invention, the laser range finder scans the surface of the patient and determines an average value for the thickness. When the entire surface is scanned, the distance measurement has a higher precision.

DESCRIPTION OF THE PREFERRED EMBODIMENTS

Figure 1:
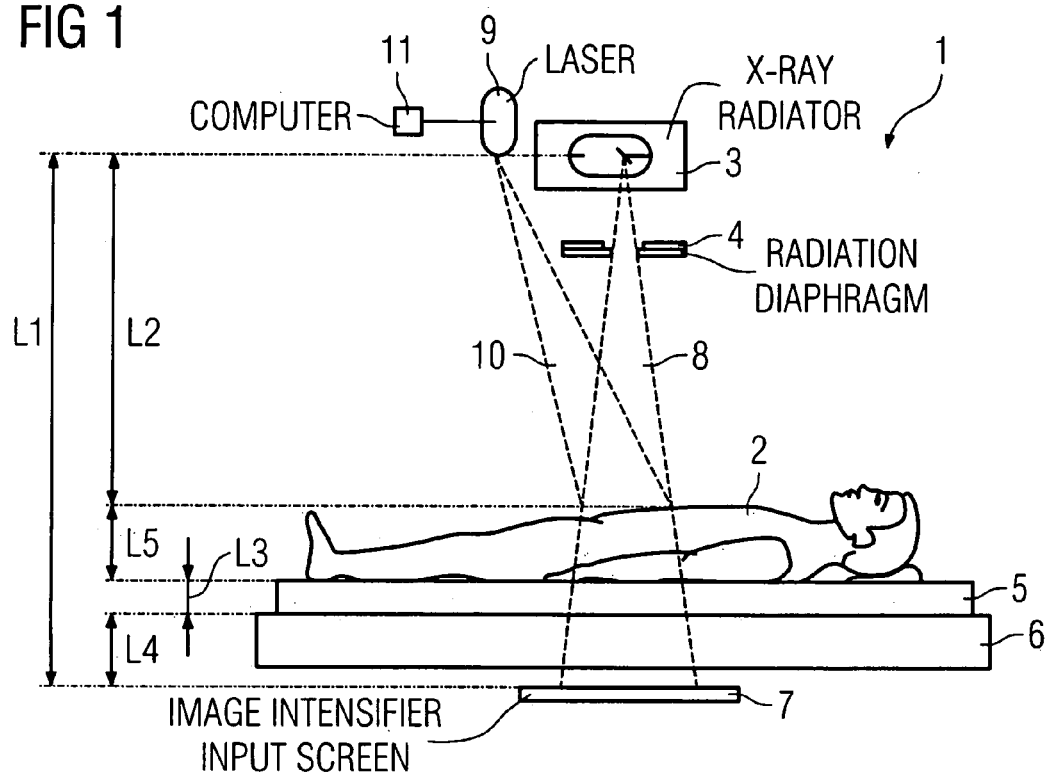
FIG. 1 is a schematic illustration of the basic components of an inventive x-ray apparatus.

FIG. 1 is a schematic representation and shows the basic components of an x-ray apparatus 1 with a patient 2, in a side view.

The x-ray apparatus 1 has an x-ray radiator 3 and a radiation diaphragm 4 disposed in the area of the x-ray radiator 3. No automatic exposure timer with a measurement chamber is present, which differs from known x-ray apparatuses.

As can be seen in FIG. 1, the patient 2 lies on a pad or support 5 that in turn rests on a tabletop 6. A film device or an image intensifier 7 is disposed beneath the table top 6, such that the x-ray field 8 emitted by the x-ray radiator 3 penetrates the patient 2 and is incident on the image intensifier input 7. A solid-state detector alternatively can be used instead of the image intensifier input 7.

A laser 9 that serves as a range finder is disposed near to and at the same height as the x-ray radiator 3. The laser 9 can measure either the direct (vertical) distance L2 between the focus or x-ray radiator 3 and the body part of the patient 2 to be examined, or alternatively a laser field 10 generated by the laser 9 can scan the entire relevant surface of the patient 2 to be examined and determine a height profile. Connected with the laser 9 is a computer device 11 that determines the thickness of the patient 2 as described below.

Figure 2:
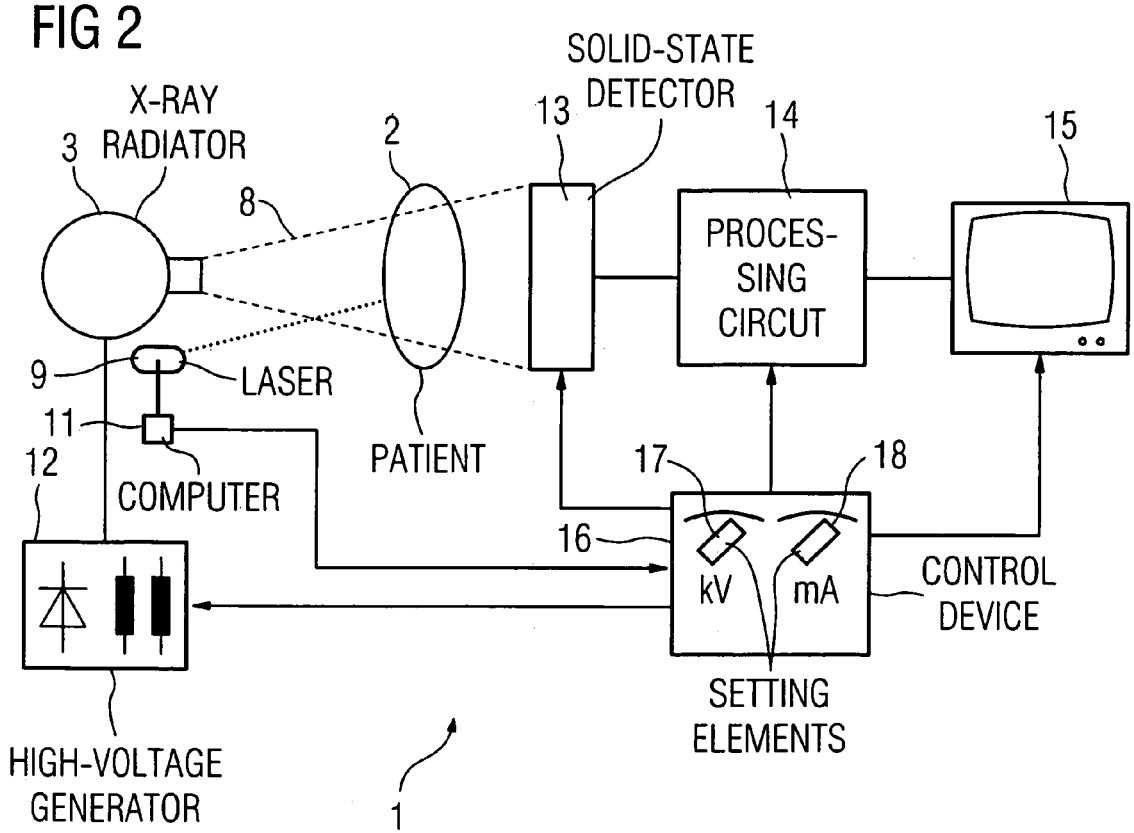
FIG. 2 is an overview of the electrical design of the entire x-ray apparatus.

FIG. 2 shows the electrical design of the inventive x-ray apparatus 1, which includes a high-voltage generator 12 that feeds the x-ray tube disposed in the x-ray radiator 3. A solid-state detector 13 emits an output signal that is supplied to a processing circuit 14 and is disposed in the beam path of the x-ray field 8, behind the patient 2.

A monitor 15 to reproduce the processed x-ray image is connected to the processing circuit 14. The processing circuit 14 can include, for example, a subtraction device, integration stage, image storage and transducer.

The x-ray apparatus 1 furthermore has a control device 16 with an automatic exposure timer that is connected with the high-voltage generator 12, the solid-state detector 13, the processing circuit 14 and the monitor 15, and supplies them with control signals. As explained below, the computer device 11 supplies to the control device 16 a signal corresponding to the thickness of the patient 2, from which the control device 16 determines the cutoff point in time for the high-voltage generator 12.

To control the high-voltage generator 12, a setting element 17 for the x-ray tube voltage kV and a setting element 18 for the x-ray tube current mA are provided on the control device 16.

When an x-ray examination is undertaken, the distance between the x-ray radiator 3 and the patient 2 is first determined by the laser 9. The focus-patient distance L2 is obtained in this manner. This measurement value is supplied to the computer device 11 that is connected with the laser 9. The height or thickness of the patient 2 is sought, which is indicated in FIG. 1 as distance L5. The thickness L3 of the support 5 as well as the distance L4 of the upper edge of the tabletop 6 from the plane of the image intensifier input 7 or the solid-state detector 13 are known and are constant geometric data that the computer device 11 can access. The film-focus distance L1 (FFA), which is the distance between the image intensifier input screen 7 and the x-ray radiator 3, is a variable but known quantity (due to the height adjustability of the x-ray apparatus 1) that is likewise supplied to the computer device 11.

The sought quantity L5 that corresponds to the height of the patient 2 results from the formula:

$$L5=L1-L2-L3-L4$$

The computer device 11 calculates the height of the patient from the known data. The height or thickness of the patient 2 is proportional to the necessary radiation dose. The computer device 11 can access a reference table, what is known as a look-up table (LUT), in which value pairs of the patient thickness and the associated radiation dose are stored. These value pairs can encompass, for example, a range of 0 to 50 cm body thickness. When the necessary radiation dose has been determined from the patient thickness, this parameter is supplied to the control device 16 for the x-ray apparatus 1, which correspondingly controls the x-ray radiator 3 and selects the appropriate exposure time.

The x-ray apparatus 1 in particular has the advantage that conventional elaborate electronics for the automatic exposure timer are not needed, and artifacts cannot be created by measurement chambers, since none are present.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray apparatus comprising:
   an x-ray radiator that emits x-ray radiation from a focus for interacting with a patient;
   an automatic exposure timer connected to said x-ray radiator;
   a laser range finder disposed to measure a focus-patient spacing between the x-ray radiator and the patient, a plurality of apparatus components having geometric data associated therewith; and
   a computer to calculate a thickness of the patient from said focus-patient distance and said geometric data and that determines a dose for said x-ray radiation for the patient dependent on said thickness, and said automatic exposure timer controlling operation of said x-ray radiator dependent on said dose determined by said computer.

2. An x-ray apparatus as claimed in claim 1 wherein said computer has a reference table stored therein with a plurality of thickness-dose pairs, and wherein said computer reads the radiation dose from said reference table in the thickness-dose pair for the thickness calculated by said computer.

3. An x-ray apparatus as claimed in claim 1 wherein said plurality of apparatus components comprise an x-ray detector having a detector surface and a patient table having a tabletop, and wherein said geometric data comprise a film-focus distance between said detector surface and said focus, and a distance between said tabletop and said detector surface.

4. An x-ray apparatus as claimed in claim 3 wherein said plurality of apparatus components include a patient support disposed on said tabletop and adapted to receive the patient thereon, and wherein said geometric data comprise a thickness of said support.

5. A method for determining a radiation dose for an x-ray examination conducted by an x-ray apparatus having an x-ray radiator that emits x-ray radiation from a focus for interacting with a patient, and a plurality of apparatus components having geometric data associated therewith, comprising the steps of:
   measuring a focus-patient distance between the x-ray radiator and the patient with a laser range finder;
   electronically automatically calculating a thickness of a body part of the patient to be examined from said focus-patient distance and said geometric data; and
   automatically electronically setting a dose for said x-ray radiation dependent on said thickness.

6. A method as claimed in claim 5 comprising electronically storing a plurality of thickness-dose pairs in a table and electronically reading said dose from said table paired with the thickness calculated in said computer.

7. A method as claimed in claim 5 comprising calculating said radiation dose using said thickness with an approximation function.

8. A method as claimed in claim 5 comprising, with said laser range finder, determining a highest point of said body part, and using said highest point for determining said focus-patient distance.

9. A method as claimed in claim 5 comprising scanning a surface of the patient with said laser range finder and, in said computer, automatically electronically calculating an average value for said thickness from the scan of the surface of the patient.

* * * * *